United States Patent
Arreola et al.

(10) Patent No.: US 10,973,679 B2
(45) Date of Patent: Apr. 13, 2021

(54) STD DETECTING CONDOM

(71) Applicants: Adam Arreola, San Jose, CA (US); Cameron R. Pye, Santa Cruz, CA (US)

(72) Inventors: Adam Arreola, San Jose, CA (US); Cameron R. Pye, Santa Cruz, CA (US)

( * ) Notice: Subject to any disclaimer, the term of this patent is extended or adjusted under 35 U.S.C. 154(b) by 610 days.

(21) Appl. No.: 15/431,409

(22) Filed: Feb. 13, 2017

(65) Prior Publication Data
US 2017/0234864 A1 Aug. 17, 2017

Related U.S. Application Data

(60) Provisional application No. 62/294,726, filed on Feb. 12, 2016.

(51) Int. Cl.
| | | |
|---|---|---|
| *A61F 6/04* | (2006.01) | |
| *A61L 31/10* | (2006.01) | |
| *A61L 31/14* | (2006.01) | |
| *G01N 33/52* | (2006.01) | |

(52) U.S. Cl.
CPC ............... *A61F 6/04* (2013.01); *A61L 31/10* (2013.01); *A61L 31/14* (2013.01); *G01N 33/528* (2013.01); *A61L 2400/10* (2013.01); *G01N 2469/10* (2013.01)

(58) Field of Classification Search
CPC ...... A61F 6/00; A61F 6/02; A61F 6/04; A61F 6/06; A61F 6/065; A61L 31/08; A61L 31/10; A61L 31/14; A61L 2400/10; G01N 33/52; G01N 33/528; G01N 2469/10; C12Q 1/00; C12Q 1/70; C12Q 1/701; C12Q 1/702; A61K 39/00; A61K 39/0006; A61K 39/118

USPC ............ 128/844, 832, 842, 830; 435/5, 7.36
See application file for complete search history.

(56) References Cited

U.S. PATENT DOCUMENTS

| | | | | |
|---|---|---|---|---|
| 5,773,234 | A * | 6/1998 | Pronovost | G01N 33/558 435/7.2 |
| 6,596,401 | B1 * | 7/2003 | Terry | C08G 18/3893 424/280.1 |
| 7,378,285 | B2 * | 5/2008 | Lambotte | G01N 33/54366 436/514 |
| 8,646,451 | B2 * | 2/2014 | Mistier | A61F 6/04 128/842 |
| 2003/0073147 | A1 * | 4/2003 | Alderete | G01N 33/558 435/7.31 |
| 2004/0231676 | A1 * | 11/2004 | Schoenfeld | A61F 6/04 128/842 |
| 2004/0248109 | A1 * | 12/2004 | Greenfield | C12N 15/1037 435/6.14 |
| 2006/0134611 | A1 * | 6/2006 | Danzy | A61F 6/04 435/5 |
| 2007/0218132 | A1 * | 9/2007 | De Simone | G01N 33/528 424/468 |

(Continued)

*Primary Examiner* — Rachael E Bredefeld
*Assistant Examiner* — Trisha Talapatra
(74) *Attorney, Agent, or Firm* — David Schneck; Thomas Schneck

(57) ABSTRACT

A condom for detection of STDs, including an interior condom surface having a control band and a test band, and an exterior condom surface that also has a control band and test band. Each test band allows binding and subsequent detection of STD antigens. A separate developing antibody produces a color change if bound to the antigen/antibody conjugate. The developing antibody may be present on the condom or applied separately after use.

16 Claims, 2 Drawing Sheets

(56) References Cited

U.S. PATENT DOCUMENTS

| | | | |
|---|---|---|---|
| 2010/0093557 A1* | 4/2010 | Kumble | G01N 33/54306 506/9 |
| 2013/0022619 A1* | 1/2013 | Rawlin | A61P 43/00 424/160.1 |
| 2013/0095227 A1* | 4/2013 | Bengtson | B29D 99/0067 427/2.3 |
| 2014/0326250 A1* | 11/2014 | Arnold | A61F 6/04 128/844 |
| 2015/0359662 A1* | 12/2015 | Netrung | A61L 31/06 128/844 |
| 2017/0172786 A1* | 6/2017 | Nguyen | A61F 6/04 |

* cited by examiner

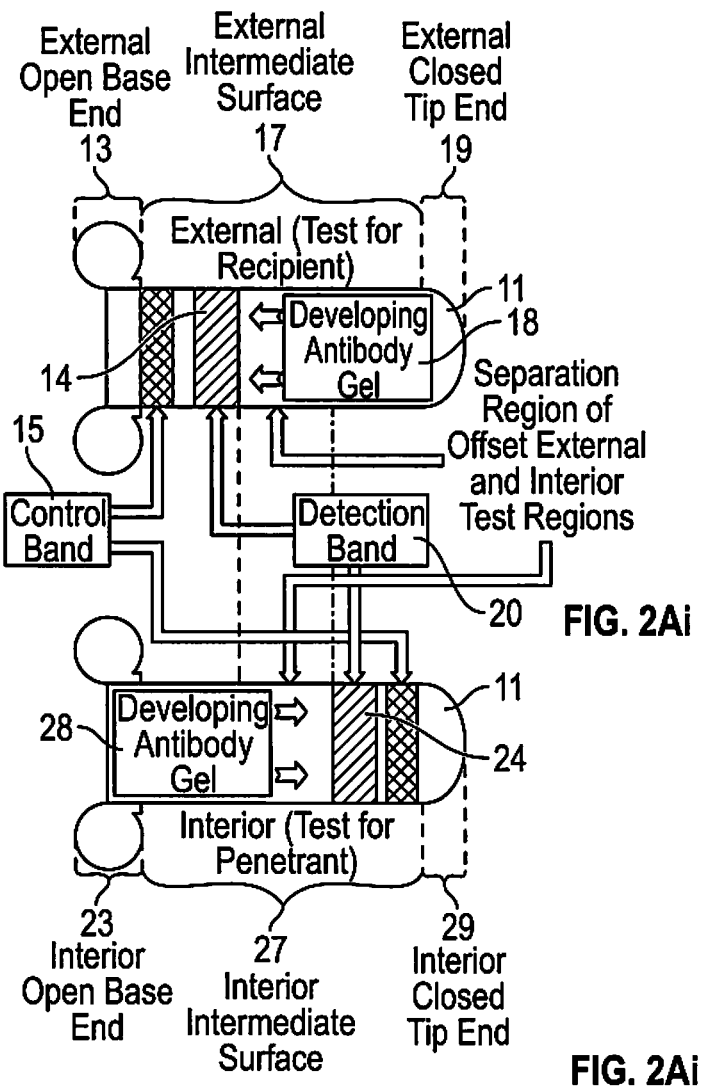
FIG. 2Ai
FIG. 2Aii
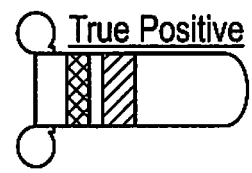
FIG. 2Bi
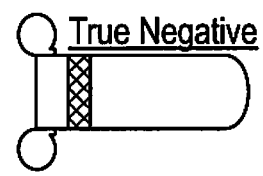
FIG. 2Bii
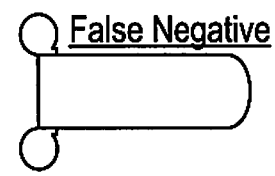
FIG. 2Biii
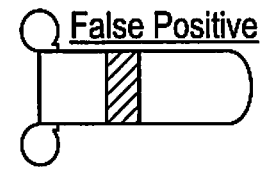
FIG. 2Biv

STD DETECTING CONDOM

CROSS-REFERENCE TO RELATED APPLICATION

This application claims the benefit from U.S. provisional application Ser. No. 62/294,726 filed Feb. 12, 2016.

TECHNICAL FIELD

The present invention relates to a condom device. More specifically the invention is a condom device able to detect infectious agents associated with sexually transmitted diseases both on the wearer of the condom and the other person who the condom is used with.

BACKGROUND OF INVENTION

Condoms are used during sexual acts both to prevent pregnancy and to prevent the spread of sexually transmitted diseases (also referred to as sexually transmitted infections). This is effected by preventing the exchange of bodily fluids between sexual partners. Currently, marketed condoms do not make the man wearing a condom or his partner informed about the presence of agents associated with sexually transmitted diseases.

SUMMARY OF INVENTION

Embodiments set out a condom that detects common sexually transmitted diseases (STDs) via a visually detectable (such as colorimetric) enzyme-linked immunosorbent assay (ELISA) strategy. This assay makes use of a reaction antibody conjugate(s) (e.g. a reaction antibody linked to a dye-activating enzyme) immobilized on the condom substrate and a developing antibody conjugate(s) (e.g. a developing antibody linked to an enzyme-reactive dye), which may be in a spatially segregated lubricating gel or development solution stored in a container for post-use application. Additionally a control band will indiscriminately bind developing antibodies to ensure device viability at the time of use. In one embodiment, the developing lubricant is separated from the detection antibodies, and distributed during intercourse. Color change in the control band and detection band will indicate a positive result.

A condom is comprised of an external closed tip end, an external open base end, an external intermediate surface extending from the closed tip end to the open base end, an interior closed tip end, an interior open base end, and an interior intermediate surface extending from said interior closed tip end to said interior open base end. When worn on a user, an inner surface is in contact with the user, and the outer surface is in contact with the user's partner. Near the closed tip end on the inner and outer surfaces are two localized bands of antibodies. Each reaction antibody is highly specific to an infectious agent associated with a sexually transmitted disease. In one embodiment, a mixture of reaction antibodies are used, each antibody component in the mixture specific to one disease associated antigen. Of the two localized bands, one band is a control band, which extends at least part way, and preferably entirely around the circumference of the condom. This band of immobilized capture antibodies is designed to react with the developing antibody even in the antigen is not present. This will demonstrate that the reagents are functioning. The second band is a test band or a detection band. This band will only undergo a visual (e.g. colorimetric) change if the targeted antigen is captured.

In this embodiment two sets of bands are used. The interior surface proximate to the closed tip of the condom has a control band and a test band. The developing antibody gel will also be on the interior of the condom, and may be included with the spermicide or lubricant used with the condom. On the exterior of the condom is a pair of bands near the open base. This also includes a control band and a test or detection band. The outside of the condom also has a developing antibody gel, which could be combined with a lubricant that is commonly used on condoms.

BRIEF DESCRIPTION OF DRAWINGS

FIG. 2Aii is a plan view of the interior of a condom embodiment.

FIG. 2Bi is a plan view of a true positive, in which both a control band and a test band show a color change.

FIG. 2Bii is a plan view of a true negative in which only the control band shows a color change.

FIG. 2Biii is a plan view of a false negative in which neither the control band nor the test band shows a color change.

FIG. 2Biv is a plan view of a false positive in which the test band shows a color change but the control band does not.

DETAILED DESCRIPTION

Condom Immobilized ELISA Strategy:

The embodiments will make use of existing visually detectable (e.g. colorigenic) ELISA technology. This visually detectable change can be through the use of fluorescent or photo luminescent dyes, in which the proximity of the immobilized capture antibody and the secondary developing antibody allow the visually detectable components to interact to produce the visual signal.

The capture enzymes are immobilized on the interior or exterior of the condom itself. Functionalization of the condom substrate will most readily be carried out using synthetic, non-latex condom formulations such as polyisoprene and polyurethane. These non-latex polymers have the added advantage of not being allergenic for users sensitive to latex. Thus a single type of material can be used for all users. In addition, the user does not have to worry about possible latex reaction from a partner.

Functionalization of polyurethane for medical devices has been demonstrated while retaining bulk properties.[2] Polyisoprene has demonstrated chemical tractability as well and could be functionalized with a variety of suitable and biologically compatible linkers that have commercially available functionality. Additionally co-polymer incorporation of biologically relevant binding partners can be introduced during initial condom production. Incorporation of primary amines or other suitable chemical handle will allow covalent attachment of commercially available biotin on a compatible linker. Either functionalization approach would be followed by normal integrity quality control measure to assure that the chemical modification has not compromised the mechanical properties of the device.

Figure 1A:
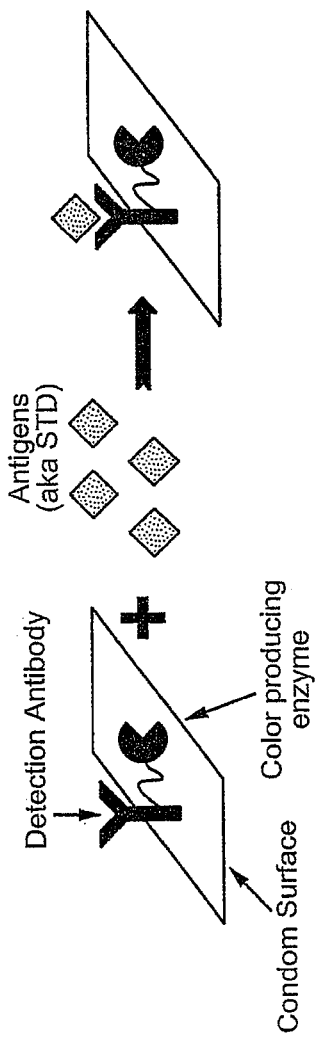
FIG. 1A is a cartoon showing a detection antibody bound to a condom surface, capturing an antigen (e.g. an agent associated with a sexually transmitted disease) and forming an immobilized detection antibody/antigen conjugate.

Detection antibodies can then be expressed as high binding streptavidin fusion proteins and effectively immobilized on the condom substrate by the tight streptavidin-biotin non-covalent interaction. The Detection antibodies will be additionally linked via a long, flexible linker sequence to a suitable ELISA enzyme (i.e. alkaline phosphatase) as illustrated in FIG. 1A. A combination of capture and detection antibodies will be used.

With reference to FIG. 1A, the immobilized antibody selective for STD associated antigen with conjugated dye activating enzyme on suitable linker is immobilized on condom surface. The condom is allowed to potentially capture the STD associated antigen during intercourse. Binding occurs if the STD associated antigen of interest is present. As illustrated, the capture antibody, immobilized on the condom surface, combines with the STD associated antigen and forms an immobilized antibody/antigen complex.

Figure 1B:
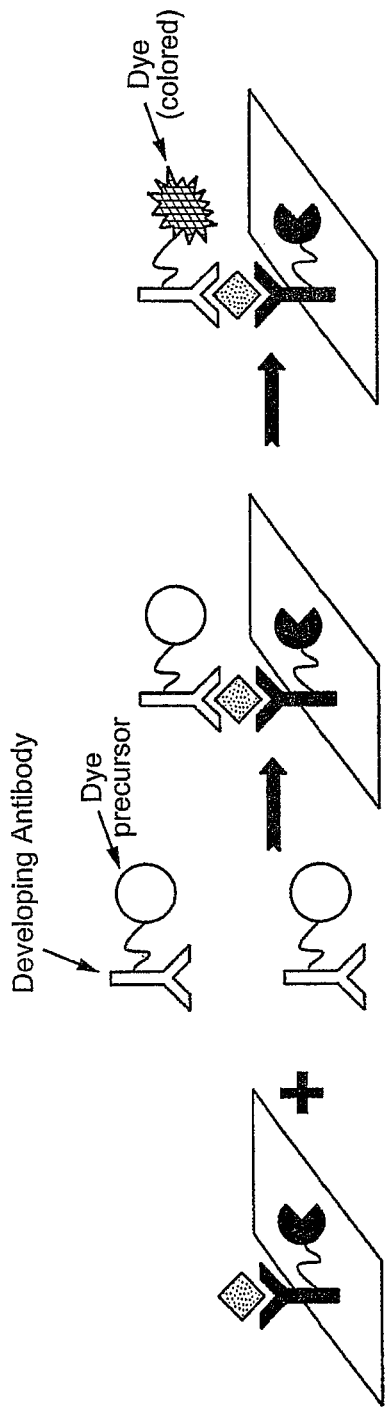
FIG. 1B is a cartoon showing the immobilized detection antibody/antigen conjugate combined with a developing antibody linked to a dye precursor, resulting in the development antibody binding to a second domain on the antibody, FIG. 2Ai is a plan view of an exterior of a condom embodiment.

In FIG. 1B the immobilized capture antibody/antigen complex is brought into contact with the development antibody. The developing antibody could be applied after the condom is removed. Alternatively the developing antibody could be included in a gel on the condom, such as a lubricant or spermicidal gel. During intercourse the gel containing the developing antibody (selective for the antigen-antibody complex) linked to the dye precursor is distributed. The resulting binding brings dye precursor and enzyme in close enough proximity to react and produce colorimetric readout.

In one embodiment, the detection antibodies will be a mixture different antibodies, each specific for commonly detectable STD. Any antigen associated with an STD that is detectable through genital bodily fluids and is able to be captured by an antibody is suitable for this assay device. This includes detection of zika virus, chlamydia (*C. trachomatis* bacteria), gonorrhea (*N. gonorrhoeae*) and trichomoniasis (*T. vaginalis* bacteria). A positive result indicates the presence of an antigen associated with one of the listed STDs Subsequent testing in a medical clinic will elucidate the exact infectious species. Control antibodies will be streptavidin fusion proteins that bind development antibodies indiscriminately (with or without the presence of antigen) to ensure the viability of the proteins and dye at the time use of the device.

In order to differentiate the separate regions of the device, separate dipping steps into baths of complementary binding proteins can be carried out. For example:
1. The condom can first be dipped into a solution containing an inert blocking protein (free streptavidin) to inactivate the portion of the condom where no detection will take place (tip of condom for exterior side).
2. The condom will dipped into a wash solution of aqueous buffer to wash off any remaining unbound blocking protein.
3. The condom will then be dipped lower than the initial blocking procedure into a solution containing the mixture of detection antibodies-streptavidin conjugates.
4. Another washing step is performed to remove excess detection antibody solution.
5. The condom is dipped to the lowest point into a solution of control antibodies to form the control band at the base of the condom for the exterior.
6. The condom is inverted and the process is repeated with for the interior condom using the inverse order of depths in order to create a mirrored pattern of bands on the interior (see FIG. 2. A)

Developing antibodies will be specific for detection antibody+bound antigen. The developing antibodies will be polyfunctionalized with an enzyme reactive colorigenic substrate (i.e. p-Nitrophenyl Phosphate (pNPP)) on a long flexible linker (i.e. polyethyleneglycol) which will allow them to be converted to their colored form upon binding with the immobilized antibody/antigen complex yielding a positive test result (FIG. 1B).

Strategies for Distribution of Developing Antibodies:

Proposed are two separate strategies for application of the developing antibody-dye conjugates to the detection and control antibodies. The first strategy is a 1-Step method where the development antibodies will be pre-distributed as a lubricating gel on the condom. During use of the condom the gel will spread over the inner our outer surface of the condom. This will bring the developing antibody, included with the lubricating/spermicidal gel into proximity with detection antibody and control antibody regions of the device. Alternatively, a solution of the development antibodies could be provided to the user to apply after the device has been used. While the first approach focuses on ease of use, the second approach focuses on reducing manufacturing steps and ensuring robust usage. In addition, it minimizes user exposure to the reagents used in the assay. Both of these strategies could be employed with the invention as described thus far though the 1-Step procedure would require an additional step in the manufacture of the condom where one selectively applies the gel to a portion of the condom exterior and interior. This could be accomplished via the described "dipping" method above after immobilization of the antibodies.

1-Step Spatially Distributed Condom Functionalization:

In order to prevent the premature reaction of the developing dye the enzyme containing antibodies will need to be spatially segregated from the developing gel. Additionally a control band with non-specific antibodies (i.e. anti-IgG) will serve to show dye and enzyme viability. For the exterior of the device this detection band and control band will be located at the base of the condom while the developing gel will be applied to the tip region of the condom. For the interior of the device the order of the gel and immobilized bands will be reversed. This will allow for easy determination of which partner's fluids contain any antigen present. Examples of test results are presented in FIG. 2. FIG. 2Ai shows the bands on the exterior of the condom. This would detect the presence of an antigen associated with the tested STDs of the recipient. FIG. 2Aii shows the interior of the condom. This would test the wearer of the condom. The condom materials suggested are at least partially see through, allowing the interior color change to be observed from the outside.

A translucent condom 11 has external and interior surface regions as shown in FIGS. 2Ai and 2Aii, respectively. In FIG. 2Ai, an external open base end 13 of condom 11 has an external surface region that has a region that is coated with control antibodies 15. An external closed tip 19 is remote from the external open base end 13 and is coated with an inert blocking protein. There is an external intermediate surface region 17 that extends from an external closed tip end 19 to the external open base end 13. The external intermediate surface region 17 is partially coated with a reaction antibody linked to a dye-activating enzyme as a detection band 20. Developing antibody gel 18 is applied to the condom exterior surface.

In FIG. 2Aii, a closed tip end 29 of a condom 11 has an interior surface region that has a region that is coated with control antibodies 15. An interior open base end 23 is remote from the interior closed tip end 29 and is coated with an inert blocking protein. There is an interior intermediate surface region 27 that extends from the interior closed tip end 29 to the interior open base end 23. The interior intermediate surface region 27 is partially coated with reaction antibody linked to a dye-activating enzyme as a detection band 20. Developing antibody gel 28 is applied to the condom interior surface. The external detection band is a first detection band 14, while the interior detection band is a second detection band 24. The first and second detection bands 14 and 24 are visually offset from each other yet visible because the condom is translucent.

The amount of false positive or negatives will likely be dependent on the concentration of the developing antibody and will be tuned to minimize both while tending towards a false positive. For the exterior of the device the act of intercourse will distribute the developing gel onto the detection and control bands in the presence of any antigen in the receiving partner's fluids. For the penetrating partner, the act of applying the device will partially distribute the gel which will be further distributed via intercourse and ejaculation. After ejaculation and in the presence of any antigen the color in the detection will develop towards the tip.

2-Step Procedure Separate Developing Solution:

Alternatively, the device could be packaged with a separate solution of developing antibody-dye conjugates. In this strategy one would use the condom as usual but after intercourse the user would manually distribute the development solution to the device exterior and then wipe any excess solution away and then allow for color to develop. The device would then be inverted the same procedure would be performed on the interior of the device. This procedure would be more cumbersome to the user but would reduce manufacturing complexity and would allow the user to ensure that the development antibodies were evenly distributed to the control and detection bands. The most likely source of user error would result in not wiping away excess developing solution which could possibly produce the appearance of color change without explicit binding. However this would likely result in a false positive which would be the more desirable outcome of device failure.

The method of manufacturing an STD detecting condom are as follows:
1. The condom is formed on mold by dip molding. As noted above, various materials are suitable for making a condom that will not allow through either sperm or infectious agents.
2. A first side of the condom is functionalized, as explained above.
3. The condom is inverted.
4. The second side of the condom is functionalized.
5. Quality control; the condom is inspected to ensure integrity (no rips, uniform thickness).
6. Antibody conjugation
   a. An initial blocking step, as set out above, to prevent inactivate the portions of the condom where no detection will take place. This creates the initial two bands.
   b. A wash step to remove blocking protein.
   c. The condom to remove lower than the initial blocking level, creating a band of detecting antibodies-strepavidin conjugates.
   d. Another washing step removes excess detecting antibody.
   e. The condom is dipped to the lowest point in a solution of control antibodies to form the control band at the base of the exterior of the condom.
7. The condom is inverted, and steps e-a are repeated in, the reverse order (i.e. step e first, step a last, the opposite of the earlier order. This creates a mirrored set of bands on the interior of the condom.
8. Once this produces is complete, the condom can be rolled up and packaged. The developing antibody can be applied after step 7 to the interior and exterior, or included separately in a separate container.

What is claimed is:

1. A surface-functionalized, elastomeric prophylactic device for sexually transmitted disease (STD) detection, being a partially translucent condom for two users who each have contact with one of the external and interior surface regions thereof comprising:
   an external closed tip end coated with an inert blocking protein;
   an external open base end coated with control antibodies;
   an external intermediate surface region having a first coating of a reaction antibody linked to a dye-activating enzyme, said external intermediate surface extending from said external closed tip end to said external open base end;
   an interior closed tip end coated with control antibodies;
   an interior open base end coated with an inert blocking protein;
   an interior intermediate surface region, having a second coating of a reaction antibody linked to a dye-activating enzyme, said interior intermediate surface region extending from said interior closed tip end to said interior open base end,
   wherein said external intermediate surface first coating of a reaction antibody linked to a dye-activating enzyme is in a first detection band offset from said interior intermediate surface second coating of a reaction antibody linked to a dye-activating enzyme in a second detection band allowing the dye-activating enzyme and antibody reactions to selectively signal a STD in the first and second offset detection bands thereby identifying a user with a STD; and
   a lubricating gel disposed on the external and interior condom surfaces and spatially segregated from the first and second reaction antibodies, said lubricating gel comprising a development compound.

2. The device of claim 1, wherein said reaction antibody is specific to a STD antigen.

3. The device of claim 1, wherein said development compound is an antibody linked to an enzyme-reactive dye wherein the antibody is specific to a STD antigen.

4. The device of claim 3, wherein the linked antibody is colorimetrically selective to an immobilized antibody-antigen complex, said antigen being specific to a STD.

5. The device of claim 4, wherein when said immobilized antibody-antigen complex on said external intermediate surface reacts with the linked antibody said enzyme reactive dye becomes activated and when said immobilized antibody-antigen complex on said interior intermediate surface reacts with the linked antibody said enzyme reactive dye becomes activated, and, when said enzyme reactive dye is activated on said external and interior intermediate surfaces, activated dye of said external intermediate surface is offset from activated dye of said interior intermediate surface.

6. The device of claim 1, wherein said lubricating gel is coated on the interior open base end and external open base end.

7. The device of claim 1, wherein said control antibodies of said external open base end extend all around said external open base end and wherein said control antibodies of said interior closed tip end extend all around said interior closed tip end.

8. The device of claim 1, wherein said first coating of a reaction antibody linked to a dye-activating enzyme is disposed on a location of the external intermediate surface spaced apart from the external closed tip end.

9. The device of claim 8, wherein said second coating of reaction antibody linked to a dye-activating enzyme is disposed on a location of the interior intermediate surface spaced apart from the interior open base end.

10. The device of claim 1, wherein said first coating of a reaction antibody linked to a dye reacting enzyme is disposed closer to the external open base end than the external closed tip end and wherein said second coating of a reaction antibody linked to a dye reacting enzyme is disposed closer to the interior closed tip end than to the interior open base end.

11. A prophylactic device, being a partially translucent condom for detecting a sexually transmitted disease comprising:
an external closed tip end coated with an inert blocking protein;
an external open base end coated with control antibodies;
an external intermediate surface region, having a first coating of a reaction antibody linked to an enzyme-linked immunosorbent assay (ELISA) enzyme, said external intermediate surface extending from said external closed tip end to said external open base end;
an interior closed tip end coated with control antibodies;
an interior open base end coated with an inert blocking protein;
an interior intermediate surface region having a second coating of a reaction antibody linked to an ELISA enzyme, said interior intermediate surface region extending from said interior closed tip end to said interior open base end,
wherein said external intermediate surface first coating of a reaction antibody linked to the ELISA enzyme in a first detection band that is offset from said interior intermediate surface second coating of a reaction antibody linked to the ELISA enzyme in a second detection band allowing ELISA enzyme and antibody reactions to selectively colorimetrically signal a sexually transmitted disease (STD) in the first and second offset detection bands upon development, thereby identifying a user with an STD
a developing compound disposed on the external and interior condom surfaces in the first and second offset detection bands.

12. The prophylactic device of claim 11, wherein said developing compound is an antibody linked to the ELISA enzymes.

13. The prophylactic device of claim 12, wherein the linked antibody is selective to an immobilized antibody-antigen complex, said antigen being specific to a STD.

14. The prophylactic device of claim 13, wherein the linked antibody is selective to an immobilized antibody-antigen complex, said antigen being colorimetrically specific to a STD.

15. The prophylactic device of claim 11, wherein said control antibodies of said external open base end extend all around said open external base end and wherein said control antibodies of said interior closed tip end extend all around said interior closed tip end.

16. The prophylactic device of claim 11, wherein said first coating of a reaction antibody linked to the ELISA enzyme is disposed closer to the external open base end than the external closed tip end and wherein wherein said second coating of a reaction antibody linked to the ELISA enzyme is disposed closer to the interior closed tip end than to the interior open base end.

* * * * *